United States Patent [19]

Nara et al.

[11] 4,162,305

[45] Jul. 24, 1979

[54] ANTIBIOTIC XK-99 AND PROCESS FOR PRODUCTION THEREOF

[75] Inventors: Takashi Nara, Tokyo; Ryo Okachi, Machida; Isao Kawamoto, Hiratsuka; Tomoyasu Sato; Tetsuo Oka, both of Machida, all of Japan

[73] Assignee: Abbott Laboratories, North Chicago, Ill.

[21] Appl. No.: 891,263

[22] Filed: Mar. 29, 1978

[30] Foreign Application Priority Data

Mar. 31, 1977 [JP] Japan .................................. 52-35215

[51] Int. Cl.$^2$ ............................................. A61K 35/00
[52] U.S. Cl. .................................... 424/120; 435/128; 435/867
[58] Field of Search ....................... 424/120; 195/80 R

[56] References Cited

U.S. PATENT DOCUMENTS

| 3,627,880 | 12/1971 | Arai et al. ............................ 424/120 |
| 4,038,383 | 7/1977 | Celmer et al. ........................ 424/120 |

Primary Examiner—Jerome D. Goldberg
Attorney, Agent, or Firm—Fitzpatrick, Cella, Harper & Scinto

[57] ABSTRACT

A novel antibacterial compound, XK-99, is produced by fermentation of an organism belonging to the genus Micromonospora. The compound is isolated from the microbial cells and culture liquor.

5 Claims, 2 Drawing Figures

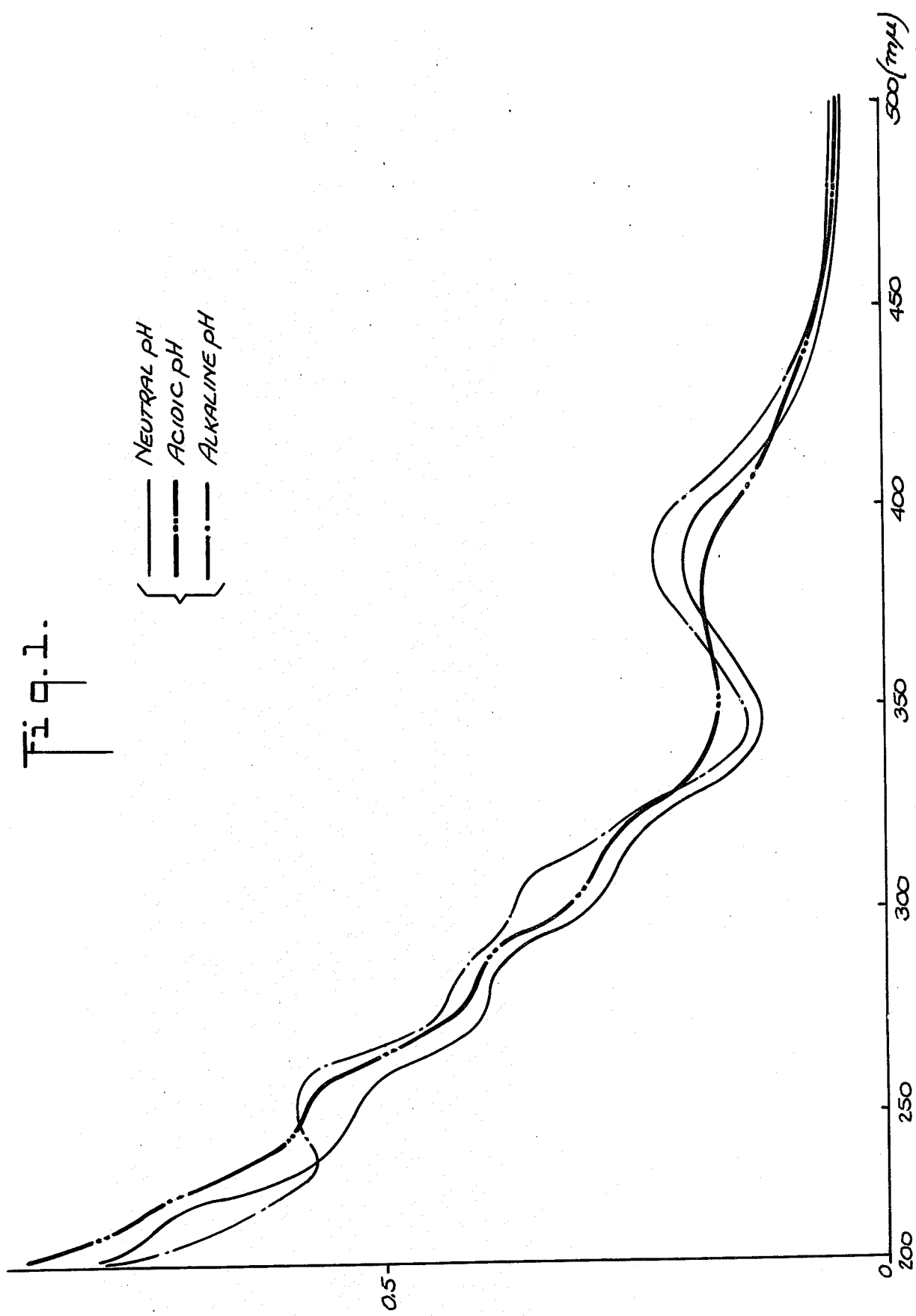

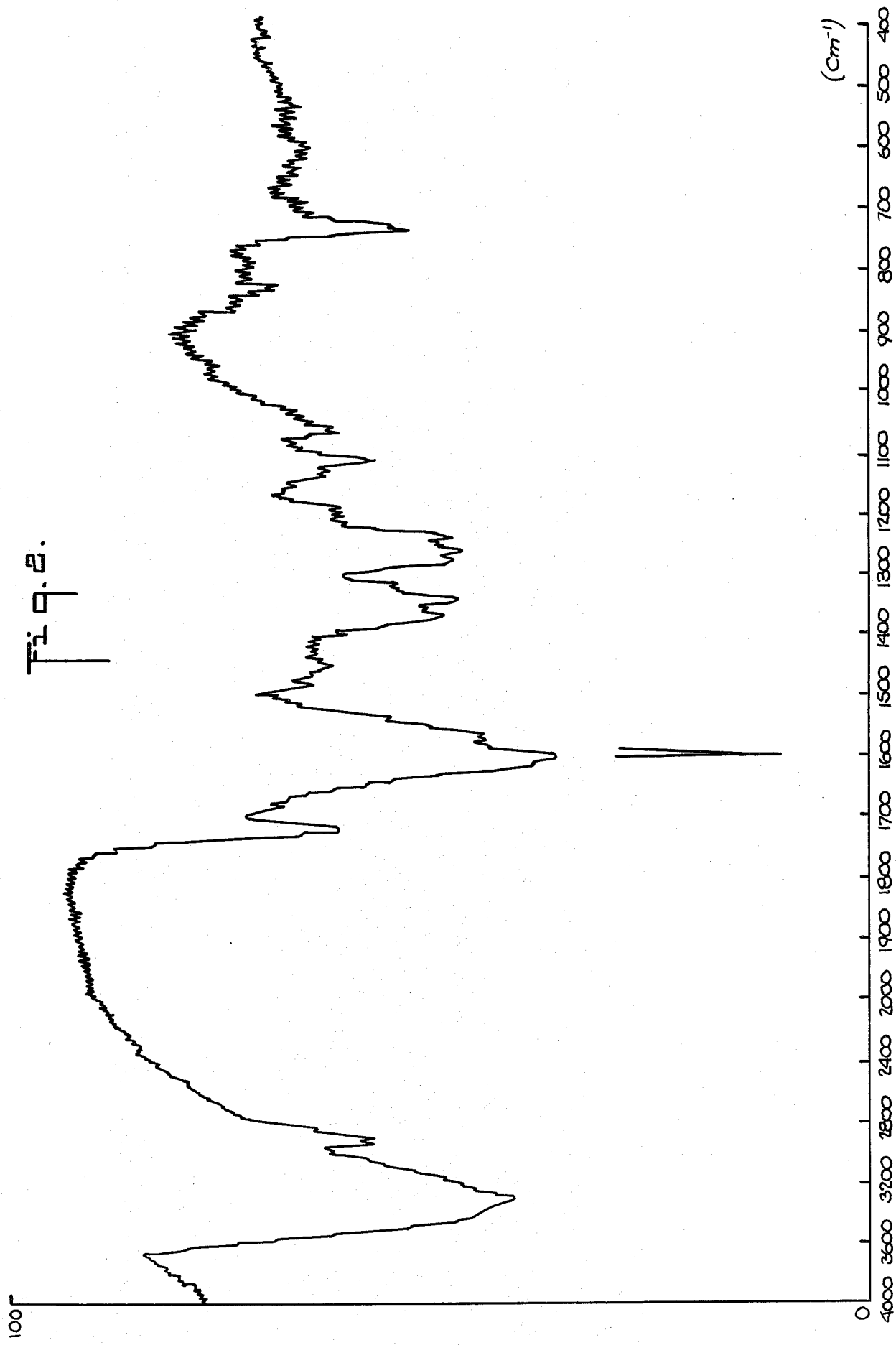

ANTIBIOTIC XK-99 AND PROCESS FOR PRODUCTION THEREOF

BACKGROUND OF THE INVENTION

The present invention relates generally to a novel antibacterial compound and a method for production thereof. More specifically, the invention relates the antibiotic XK-99 and the fermentative production thereof using a novel strain of microorganism belonging to the genus Micromonospora.

Antibacterial compounds exhibiting a broad spectrum activity against Gram-positive and Gram-negative bacteria are always in demand. To this end, a new strain of microorganism (hereinafter sometimes referred to as the "MK-99 strain") has been isolated from farm soil at Iwato in Komae City, Tokyo, Japan. In a biologically pure culture, the MK-99 strain produces a novel antibacterial compound, XK-99, which exhibits broad spectrum activity.

SUMMARY OF THE INVENTION

In accordance with the present invention, the antibiotic XK-99 is produced by culturing a microorganism belonging to the genus Micromonospora which is capable of producing said antibiotic, in a nutrient medium until substantial antibacterial activity is detected in the culture liquor; and thereafter isolating XK-99 therefrom.

DESCRIPTION OF THE INVENTION

The MK-99 Strain

Morphological features and physiological properties of the MK-99 strain are as follows:

I. Morphological features

The MK-99 strain grows better on a natural organic medium, than on a synthetic medium. The strain fails to form true aerial mycelia on common agar medium, and substrate mycelia are raised and folded, and orange-colored. Microscopically the substrate mycelium on agar medium or obtained by liquid culture are well developed, about $0.5\mu$ in diameter, relatively short and branched in many directions around the tips of hyphae, and composed of short lengths of fragmented hyphae in liquid culture. Black spores are borne singularly on a short sporophore simply branched from the substrate mycelia or sometimes sessile on the substrate mycelia. Dichotomously borne spores are observed at the outermost end of hyphae. When viewed by electron microscopy, a mature spore is about $0.8-1.2\mu$ in diameter, spherical or oval, and has a smooth surface.

II. Culture characteristics

The degree of growth, color, etc. are set forth below, when the MK-99 strain was cultured on various media at 27° C. for two weeks. The color indications are given according to the classifications in the Color Harmony Manual (Container Corporation of America). The color given is that of the mycelial web on the colony surface, and the color of the face and back of substrate mycelia.

| | | |
|---|---|---|
| 1. | Czapek's agar medium: | no growth |
| 2. | Glucose asparagine agar medium: | no growth |
| 3. | Starch agar medium: | no growth |
| 4. | Glycerol asparagine agar medium: | no growth |
| 5. | Nutrient agar medium: | |
| | growth: | poor, flat |
| | color: | Brite Melon Yellow (3ia) |
| | soluble pigment: | Light Yellow (1½ea) |
| 6. | Egg agar medium: | |
| | growth: | poor, flat |
| | color: | Light Wheat (2ea) |
| 7. | Oat meal agar medium: | |
| | growth: | normal smooth |
| | color: | Orange (4ia) |
| 8. | Yeast-malt agar medium: | |
| | growth: | moderate, raised |
| | color: | Luggage Tan (4ne) |
| | soluble pigment: | Amber (3nc) |
| 9. | Bennett's agar medium: | |
| | growth: | moderate, plicate |
| | color: | Orange Rust (4pe) |
| | soluble pigment: | Light Yellow (1½ea) |
| 10. | Emerson's agar medium: | |
| | growth: | moderate, flat |
| | color: | Russet Orange (4pc) |
| | soluble pigment: | Amber (3pc) |
| 11. | Glucose-yeast agar medium: | |
| | growth: | moderate, flat, black spore layer slightly formed. |
| | color: | Russet Orange (4nc) |
| | soluble pigment: | Amber (3pc) |
| 12. | Hickey-Tresner's agar medium: | |
| | growth: | moderate, plicate |
| | color: | Russet Orange (4pc) |
| | soluble pigment: | Light Yellow (1½ea) |
| 13. | Peptone-yeast-iron agar medium: | |
| | growth: | poor, flat |
| | color: | Brite Yellow (3ia) |
| | soluble pigment: | Light Yellow (1½ea) |
| 14. | Tyrosine agar medium: | |
| | growth: | poor, flat |
| | color: | Brite Yellow (3ia) |
| | soluble pigment: | Rust Brown (5pg) |

III. Physiological properties

The following physiological properties are determined by observation after two weeks of culturing at 27° C., except temperature which is given after 5 days of culturing and action upon milk and cellulose which are determined after one month of culturing.

1. Utilization of carbon source: starch is well assimilated; D-glucose, D-fructose, saccharose, D-xylose, and mannose are relatively well assimilated; but D-arabinose, glycerol, D-lactose, L-inositol, D-raffinose, L-rhamnose, α-melibiose, D-melizitose, salicin, dulcitol, sorbitol, and L-sorbose are not assimilated. D-galactose and D-mannitol are poorly assimilated.
2. Liquefaction of gelatin: very slowly liquefied
3. Action upon milk: no change
4. Cellulose decomposition: slightly observable
5. Starch hydrolysis: observed
6. Nitrate reduction: none
7. Tyrosinase formation: observed
8. Melanoid formation: observed
9. Optimum pH: 6.8–8.0
10. Optimum temperature: 30° C.–38° C.

The MK-99 strain is a mesophilic bacterium incapable of forming true aerial mycelia on agar medium, and bears single spores on substrate mycelia. By analysis of amino acids, the strain contains hydroxy and mesodiaminopimelic acid in the cell wall; and by analysis of sugars, contains arabinose and xylose in the whole cell. Therefore, the strain is classified as an Actinomycetales belonging to the genus Micromonospora.

Luedemann et al. state that morphological characteristics such as branching mode of hyphae and sporophore; and carbohydrate utilization pattern are useful for the classification of the genus of Micromonospora. According to Bergey's Manual of Determinative Bacteriology (8th edition), the aerobic species of Micromonospora are classified into four main groups, that is, two groups according to utilization of α-melibiose; and into two other groups for which carbohydrate utilization is lacking, these latter groups being by pigment characterization. Each of the four main groups are further classified into subgroups. The present strain fails to utilize α-melibiose, L-rhamnose, and D-raffinose, and is closer to *Micromonospora purpurea* according to the classification on the basis of carbohydrate utilization, but is very different therefrom in branching mode of hyphae, formation of spores having smooth surfaces, pigments produced, etc. When the MK-99 strain is compared with the other strains of the genus by morphological characteristics, no mycelial branching as that of *Micromonospora narashinoensis*, for example, is observed. On the other hand the instant strain is very similar to *Micromonospora melanosporea* in the relatively short branching in cluster around the tips of hyphae, smooth surface of spore, etc. Though the classificational position depends upon a preference to either morphological characteristics or utilization of carbon source, the MK-99 strain has been classified according to the morphological characteristics and, therefore, is determined to belong to the species *Micromonospora melanosporea*. *Micromonospora melanosporea* grows well on a starch-inorganic salt agar medium, whereas the MK-99 strain fails to grow on this substrate. *Micromonospora melanosporea* has a milk coagulation action and a peptonization action, whereas the MK-99 strain does not. *Micromonospora melanosporea* utilizes α-melibiose and D-lactose, whereas the MK-99 strain does not. Furthermore, the MK-99 strain produces soluble amber pigments on various media. In view of the foregoing, the present strain is classified as a subspecies of *Micromonospora melanosporea*, and is named *Micromonospora melanosporea* subspecies komaensis.

Cultures of *Micromonospora melanosporea* subsp. komaensis have been deposited with the Fermentation Research Institute Agency of Industrial Science and Technology, Chiba City, Japan, and the United States Department of Agriculture, Peoria, Ill. which deposits have been respectively accorded accession numbers FERM-P No. 3954 and NRRL 11100. Subcultures of these deposits are available to the public.

As is the case with other strains of Actinomycetes, the microorganisms useful in carrying out the present invention can be mutated by artificial means such as ultraviolet irradiation, X-ray irradiation and use of various mutation inducing chemicals in known manner to enhance the production of metabolic products. Accordingly the present invention contemplates use of such mutants insofar as they have the ability to produce XK-99.

Generally, conventional methods for culturing microorganisms of the Actinomycetes may be employed for culturing the MK-99 strain and various nutrient sources are acceptable. For example, glucose, starch, mannose, fructose, sucrose, molasses, etc. may be used alone or in combination as a carbon source. Furthermore, hydrocarbons, alcohols, organic acids, and the like can be used as a carbon source, depending upon the ability of the strain to assimilate these sources. Ammonium chloride, ammonium sulfate, urea, ammonium nitrate, sodium nitrate, etc. can be used as inorganic and organic nitrate sources; and peptone, meat extract, yeast extract, dried yeast, corn steep liquor, soybean powders, casamino acid, soluble vegetable protein, cotton seed cakes, etc. are used alone or in combination as a natural nitrogen source. In addition, inorganic salts such as sodium chloride, potassium chloride, calcium carbonate, phosphate, etc. can be added to the medium if necessary, as well as organic or inorganic materials capable of promoting growth of the strain and/or the production of XK-99.

A liquid culturing method, particularly a submerged stirring culturing method, is most suitable for culturing the strain. Culturing is preferably carried out at a temperature of 25°–40° C. and around neutral pH for 4 to 7 days. Under such conditions, the antibiotic XK-99 is accumulated in the culture broth. When the amount of the antibiotic in the culture broth reaches a maximum, culturing is terminated, and the desired product is isolated from the broth and microbial cells.

Those procedures normally used for isolation of microbial metabolic products from culture broth may be utilized for the isolation and purification of XK-99. Since XK-99 is slightly soluble in water, soluble in lower alcohols such as methanol, ethanol, n-butanol, etc., and insoluble in benzene, chloroform, ethyl acetate, purification methods based on these properties is employed. That is, extraction of active components from cell bodies by methanol, HP-10 resin column chromatography, silica gel column chromatography, Sephadex LH-20 column chromatography, etc. can be used in an appropriate combination.

For example, after the completion of culturing, the culture broth is admixed with a filter aid, and is subjected to filtration using a filter press to separate the cell bodies from the culture liquor. The cell bodies are thoroughly washed with water, then admixed with an equal volume of methanol, and vigorously stirred for 30 minutes, whereby most of the active component is extracted into the methanol. After removal of the cell bodies by filtration, the cell bodies are again washed with a small amount of methanol. The filtrate and the methanol washes are joined together, and concentrated under reduced pressure to distill away methanol. The remaining aqueous layer is thoroughly mixed with hexane, and then the hexane layer is removed. The residual aqueous layer is concentrated under reduced pressure to distill away the contaminating hexane, and then adjusted to pH 6.8 with caustic soda. The resulting aqueous solution is passed through a column packed with HP-10 resin [made by Mitsubishi Kasei Kogyo K.K.] whereby the active component is adsorbed onto the resin. The resin is washed with water and the effluent liquor and washing water are discarded. The resin is then subjected to elution with an aqueous 80% methanol solution. Eluted fractions are bioassayed with *Staphylococcus aureus* to collect those fractions exhibiting antibacterial activity. The fractions are combined and concentrated to dryness under reduced pressure, to obtain a crude powder of XK-99.

For further purification of the crude powder, silica gel powder is suspended in a mixed solvent of n-butanol:acetic acid:water, 3:1:1, (all ratios are by volume), packed in a glass column, and thoroughly washed with the foregoing solvent. The crude powder of XK-99 is charged onto the silica gel column, and the column is subjected to continuous elution using the same mixed solvent. Eluted fractions are individually collected by a fraction collector, and the individual fractions are bioassayed with *Staphylococcus aureus*. Those fractions having antibacterial activity are collected, combined and concentrated under reduced pressure. The concentrate is then changed into a column packed with Sephadex LH-20 (trade mark, made by Pharmacia, Sweden) and the column is washed with an aqueous 80% methanol solution. When the column is subjected to elution with the same aqueous 80% methanol solution, XK-99 is eluted. Fractions containing XK-99 are collected by bioassay with *Staphylococcus aureus*, and are combined and concentrated to dryness under reduced pressure, whereby a purified preparate of XK-99 is obtained.

The antibiotic

The physico-chemical properties of XK-99 thus obtained are as follows. The material is an amorphous reddish brown powder having an elemental analysis (found) of 58.24% C, 4.57% H and 9.89% N, and a molecular weight of 390 presumed by mass spectrum. The melting point is more than 250° C., and decomposition occurs without exhibiting a distinct melting point.

FIG. 1 illustrates the ultraviolet absorption spectrum of XK-99 measured in methanol solution, where the spectrum at neutrality is plotted by a full line; at the acidic side by a one dot and one short line; and at the alkaline side by two-dots-and-one short line. For altering the pH hydrochloric acid or aqueous caustic soda solution is used.

Optical rotation of the antibiotic in methanol solution is $[\alpha]_D^{24} = -360°$ (c=0.1, methanol).

FIG. 2 illustrates the infrared absorption spectrum of XK-99 by potassium bromide tablet method. As is apparent from FIG. 2, the maximum absorption is exhibited at the following wave numbers: 3400, 2900, 1720, 1600, 1345, 1370, 1280, 1260, 1240, 1115, 1070, 830 and 740 (cm$^{-1}$).

The compound is soluble in methanol and ethanol, slightly soluble in water, and insoluble in such organic solvents as benzene, chloroform, ethyl acetate, n-hexane, etc.

Rf values on paper chromatography and thin layer chromatography of XK-99 using various developers are given in the following Tables 1 and 2.

Table 1

| Paper chromatography of XK-99 | |
|---|---|
| Developer | Rf value |
| 1. Aqueous 20% ammonium chloride solution | 0.0 |
| 2. Water-saturated n-butanol | 0.15 |
| 3. n-butanol:acetic acid:water (3:1:1) | 0.45 |
| 4. Water-saturated ethyl acetate | 0.0 |
| 5. Water-saturated n-butanol containing 2% p-toluenesulfonic acid and 2% piperidine | 0.28 |

Filter paper: Toyo Roshi No. 51 (2 × 40 cm) trade name, Toyo Roshi Co., Inc., Japan)
Development: 28° C. ascending method; Developing time: 3 hours for 1 and 4, and 15 hours for 2, 3 and 5.
Detection: Bioautography with *Staphylococcus aureus*.

Table 2

| Thin layer chromatography of XK-99 | |
|---|---|
| Developer | Rf value |
| 1. Upper layer of n-butanol:acetic acid: water (4:1:5) | 0.50 |

Table 2-continued

| Thin layer chromatography of XK-99 | |
|---|---|
| Developer | Rf value |
| 2. Lower layer of n-butanol:acetic acid: water (4:1:5) | 0.00 |
| 3. Upper layer of n-butanol:pyridine: water (10:1:10) | 0.30 |
| 4. Lower layer of n-butanol:pyridine: water (10:1:10) | 0.20 |
| 5. Diisobutylketone:acetic acid:water (8:5:1) | 0.70 |

Thin layer: cellulose (Eastman, # 13254, 20 cm × 20 cm)
Development: 4 hours at room temperature, ascending method
Detection: Bioautography with *Staphylococcus aureus*

The antibacterial spectra of XK-99 against various microorganisms is given in the following Table 3 wherein the minimum inhibitory concentration (MIC) (mcg/ml) is determined by the agar-dilution method at pH 7.0.

Table 3

| Antibacterial spectra of XK-99 | |
|---|---|
| Microorganisms tested | MIC (γ/ml) |
| *Staphylococcus aureus* KY 4279 | 0.7 |
| *Bacillus subtilis* KY 4273 | 10.5 |
| *Bacillus cereus* KY 3308 | 0.35 |
| *Streptococcus faecalis* KY 4280 | >100 |
| *Sarcina lutea* KY 4122 | 5.3 |
| *Neisseria catarrhalis* KY 4282 | 0.18 |
| *Alkaligenes faecalis* KY 3101 | 0.7 |
| *Klebsiella pneumoniae* KY 4275 | 2.7 |
| *Salmonella typhosa* KY 4278 | >100 |
| *Proteus vulgaris* KY 4277 | >100 |
| *Proteus mirabilis* KY 8467 | 83.3 |
| *Escherichia coli* KY 4271 | 0.7 |
| *Pseudomonas alkaligenes* KY 4656 | 1.4 |
| *Vibrio percolans* KY 4174 | 0.35 |
| *Mycobacterium avium* KY 3851 | 1.4 |
| *Mycobacterium coda* KY 3852 | 0.7 |
| *Mycobacterium smegmatis* KY 3848 | 0.7 |
| *Mycobacterium phlei* Ky 3486 | <0.03 |
| *Shigella sonnei* KY 4281 | 2.7 |

The anti-transplanted tumor activity of XK-99 has been investigated as follows:

Solid-type Sarcoma 180 cells (5×10$^6$) were subcutaneously transplanted into male dd-strain mice having an average body weight of 19±1 g. One month thereafter a sample of XK-99 suspended in 3% carboxymethylcellulose was administrated interperitonally. After 7 days, the tumor sizes were measured and compared with those of a control. The results are given in the following Table 4.

Table 4

| Anti-transplanted tumor activity of XK-99 | | |
|---|---|---|
| Dosage of XK-99 administered (mg/Kg) | Anti-transplanted tumor activity (T/C*) | Number of leucocytes |
| 25 | 0.28 | 8060 |
| 12.5 | 0.45 | 7470 |
| 6.25 | 0.64 | 7770 |
| 3.125 | 0.57 | 6710 |

*T/C = Average size of tumor of mice administered with XK-99 / Average size of tumor of control mice As is evident from the foregoing, XK-99 has a strong antibacterial activity against a broad range of Gram-positive and negative microorganisms, and shows a remarkable therapeutical effect upon solid type tumor of Sarcoma 180. However, the compound appears to be highly toxic and abnormal kidneys and livers were observed in test mice. Therefore, the base compound is useful as a topical antibacterial agent for cleaning and sterilizing laboratory glassware and surgical instruments and may also be used in combination with soaps, detergents and wash solutions for sanitation purposes.

As for other antibacterial substances produced by microorganisms belonging to the genus Micromonospora, the so called ansamacrolide antibiotic group such as halomicin A, B, C and D (U.S. Pat. Nos. 3,511,909, 3,880,839, etc.), rifamycin S, SV (U.S. Pat. No. 3,884,763, etc.) are known. As anti-tumor antibiotics, actinomycin complex (U.S. Patent No. 3,954,970, etc.), and the like are known. Furthermore, among the antibiotics produced by the other actinomycetes, those showing properties similar to those of XK-99 include adriamycin [F. Arcrome et al.: Tetrahed. Lett., 13 1007 (1969), etc.], daunomycin (British Patent No. 1,003,383, etc., and acrasinomycin [T. Oki et al.: J. Antibiotics 28 830 (1975), etc.].

A comparative study of XK-99 with these antibiotics was conducted according to several procedures. The results are given in the following Table 5.

Table 5

| Antibiotic | Antibacterial activity[1] | | | Rf[2] | | |
|---|---|---|---|---|---|---|
| | [A] | [B] | [C] | 2 | 3 | 4 |
| Actinomycin D | 0.084 | 0.021 | 4 | 0.85 | 0.90 | 0.60 |
| Rifamycin S | <0.0045 | 0.09 | <0.05 | 0.78 | 0.88 | 0.63 |
| Halomicin B | <0.0045 | 0.09 | <0.05 | 0.80 | 0.85 | 0.90 |
| Adriamycin | 5.6 | 0.70 | 8 | 0.40 | 0.28 | 0.0 |
| Daunomycin | 2.8 | 0.70 | 4 | 0.48 | 0.45 | 0.0 |
| Acrasinomycin | 0.68 | 0.17 | 4 | 0.83 | 0.0 | 0.90 |
| XK-99 | 0.7 | 10.5 | 0.067 | 0.15 | 0.45 | 0.0 |

[1]Antibacterial activities (minimum inhibition concentration, MIC, γ/ml) of the individual antibiotics measured simultaneously according to agar dilution method against [A] *Staphylococcus aureus* and [B]*Bacillus subtilis*, and [C] ratio of [A] to [B].
[2]Rf values of the individual antibiotics on paper chromatography, where 2, 3 and 4 correspond to the solvents 2, 3 and 4 shown in Table 1.

As is evident from the foregoing, there are great differences in the antibacterial activity against *Bacillus subtilis* between the known antibiotics and XK-99. Furthermore, there are significant differences in ratio [C] of the antibacterial activity against *Staphylococcus aureus* to that against *Bacillus subtilis* between other antibiotics than those of the ansamacrolide group, such as rifamycin, etc. and XK-99. The antibiotics of the ansamacrolide group showing similar values in the ratio [C] of antibacterial activities are obviously different from XK-99 in the Rf values on the paper chromatography. Also, from the foregoing table, the antibiotics of the anthracycline group, such as adriamycin, etc., are quite different in the ratio [C] of the antibacterial activities from XK-99. Moreover, the latter antibiotics have the common property of turning bluish violet at the alkaline side and yellow at the acidic side by changing the pH of the solutions. On the other hand, XK-99 does not change color upon altering the pH of the solution; and, thus, XK-99 is evidently different from these well known antibiotics. Thus, XK-99 is a novel antibacterial composition of matter.

Certain specific embodiments of the present invention are illustrated by the following representative examples.

EXAMPLE 1

In this example, *Micromonospora melanosporea* subsp. komaensis, MK-99 strain (NRRL 11100; FERM-P No. 3954) is used as a seed microorganism, and a medium containing 2 g/dl glucose, 0.5 g/dl peptone, 0.5 g/dl yeast extract and 0.1 g/dl calcium carbonate (pH 7.2 before sterilization) is used as a first seed medium.

One platinum loop of the seed microorganism is inoculated into 50 ml of the seed medium in a large test tube, and cultured at 30° C. for 3 days. Then, 10 ml of the seed culture liquor is inoculated into 30 ml of a second seed medium in a 300-ml Erlenmeyer flask. The composition of the second seed medium is the same as that of the first. The second seed culture is conducted at 30° C. with shaking for two days. Then, 30 ml of the second seed culture liquor is inoculated into 300 ml of a third seed medium in a 2-L. Erlenmeyer flask provided with a baffle. The composition of the third seed medium is the same as that of the first. The third seed culture is carried out at 30° C. with shaking for two days.

The capacity of three flasks (0.9 L.) of the third seed medium is inoculated into 15 L. of a main fermentation medium in a 30-L. stainless steel jar fermentor. The main fermentation medium comprises 3 g/dl lactose, 1 g/dl soluble vegetable protein, 0.5 g/dl NZ-amine type A, 0.5 g/dl yeast extract, 5 mg/L. of $CuSO_4.5H_2O$, 5 mg/L. of $MnCl_2.4H_2O$, 5 mg/L. of $ZnSo_4.7H_2O$, 1 mg/L. of $CoCl_2.6H_2O$, 20 mg/L. of $FeSO_4.7H_2O$ and 0.2 g/dl $CaCO_3$ (pH 7.3 s admixed with about 1 kg of Radiolite #600 filter aid (made by Showa Kagaku Kogyo K.K.), and the cell bodies are filtered off while reserving the filtrate. The cell bodies and filter aid are washed thorougly with about 10 L. of water and then suspended in 5 L. of methanol, and vigorously stirred for about 30 minutes. XK-99 usually is liberated from the cell bodies through this operation, and the methanol solution and the cell bodies are separated from each other by filtration. However, to insure maximum recovery, the cell bodies are again suspended in 5 L. of methanol, and stirred for 30 minutes. The cell bodies are removed from the solution by filtration, and the resulting filtrate is joined with the initial methanol solution to obtain about 10 L. of methanol solution containing XK-99, which is then concentrated to about 500 ml under reduced pressure, and admixed with 300 ml of n-hexane and vigorously agitated. After standing, the hexane layer is removed and the residue is again admixed with 300 ml of hexane, vigorously agitated to remove the hexane-soluble impurities, and then admixed with 200 ml of ethyl ether and vigorously agitated. After standing, the ether layer is removed. The ether extraction is again repeated to remove ethyl ether-soluble impurities. The resulting aqueous layer residue is diluted with 1 L. of distilled water, and adjusted to pH 6.8. This aqueous solution is then passed through a glass column packed with 100 ml of HP-10 resin (made by Mitsubishi Kasei Kogyo K.K.) to adsorb the active component on the resin. After the column is washed with about 300 ml of distilled water, the effluent fraction and washing water are discarded. Then, the column is subjected to elution with an aqueous 80% methanol solution containing 0.2 N ammonia.

The eluate is collected in 10 ml fractions by a fraction collector, and about 300 ml of 80% ammoniacal methanol is passed through the column. Antibacterial activity of the eluted fractions is detected according to a paper disc method using *Staphylococcus aureus*, whereby activity is found in test tubes of fraction numbers 8–15. These fractions are combined and concentrated to 2 ml under reduced pressure. The resulting solution is then charged into a glass column packed uniformly with about 150 ml of Sephadex LH-20 suspended in methanol and the column is then eluted with methanol at a flow rate of 40 ml/hr. The eluate is collected as 5 ml fractions, and the antibacterial activity of each fraction is determined according to a paper disc method using *Staphylococcus aureus*. Antibacterial activity is found in the fractions numbered 32-35, which are combined, and concentrated under reduced pressure to distill away methanol whereby XK-99 is obtained as a reddish brown powder. The yield is 15 mg and the minimum inhibition concentration against *Staphylococcus aureus* is 0.7γ/ml.

EXAMPLE 2

In this example, the procedures of Example 1 are repeated through the main fermentation. After the completion of culturing, the culture broth is admixed with a filter aid, and filtered. The filtrate (about 12 L.) is adjusted to pH 7.0 with 2 N hydrochloric acid, and is then passed through a column packed with 1 L. of HP-10 resin suspended in water, whereby the XK-99 component liberated extracellularly during culturing and accumulated in the culture filtrate is adsorbed and retained on the HP-10 resin. After passage through the column, the resin is washed with about 3 L. of distilled water, and the effluent liquor and washing water are discarded. Then, the column is subjected to elution with an aqueous 80% methanol solution containing 0.2 N ammonia, and each 100 ml of the eluate is collected as fractions and the antibacterial activity thereof is determined according to a paper disc method using *Staphylococcus aureus*. Antibacterial activity against *Staphylococcus aureus* is found in fraction numbers 9-17. These fractions are combined and concentrated to about 10 ml under reduced pressure.

The resulting residue is charged into a column packed uniformly with about 500 ml of cellulose (AVICEL, made by Funakoshi Yakuhin K.K.) suspended in a mixed solvent of n-butanol:acetic acid:water (3:1:1). Then, the column is subjected to elution with the same mixed solvent at a flow rate of 60 ml/hr. Eluate fractions of 20 ml each are collected and the activity thereof is detected according to a paper disc method using *Staphylococcus aureus*. Activity is found in fraction numbers 42-56. These fractions are combined, and concentrated to 2 ml under reduced pressure.

The resulting residue is charged into a glass column packed uniformly with 150 ml of Sephadex LH-20 suspended in methanol. Then, the column is subjected to elution with methanol at a flow rate of 40 ml/hr, and the eluate is collected in 5 ml fractions. Antibacterial activity of the fractions is determined by paper disc method using *Staphylococcus aureus*, whereby activity is found in fraction numbers 34-40. These fractions are combined, and concentrated under reduced pressure to distill away methanol to obtain XK-99 as a reddish brown powder. The XK-99 thus obtained is identical with that obtained from the cell bodies, and its yield is 17 mg. Minimum inhibition concentration against *Staphylococcus aureus* is 0.7γ/ml.

What is claimed is:

1. XK-99, an antibacterial composition of matter characterized by:
   (a) a molecular weight of 390;
   (b) a melting point about 250° C. with decomposition;
   (c) Specific Rotation: $\alpha_D^{24} = -360°$ (C=0.1 methanol);
   (d) ultraviolet absorption spectra essentially as shown in FIG. 1;
   (e) infrared absorption spectrum essentially as shown in FIG. 2; and
   (f) a found elemental analysis of 58.24% C, 4.57% H and 9.89% N.

2. A method for producing XK-99 as defined in claim 1 which comprises culturing a microorganism having the identifying characteristics of *Micromonospora melanosporea* subsp. komaensis NRRL 11,100 in a nutrient medium until substantial antibacterial activity is detected in the culture liquor.

3. A method according to claim 2 wherein said XK-99 is isolated from the culture liquor.

4. A method according to claim 2 wherein said XK-99 is isolated by extraction from the cell bodies.

5. A method according to claim 2 wherein said culturing step is carried out at from 25° to 40° C. and approximately neutral pH for 4 to 7 days.

* * * * *

UNITED STATES PATENT AND TRADEMARK OFFICE
CERTIFICATE OF CORRECTION

PATENT NO. : 4,162,305
DATED : July 24, 1979
INVENTOR(S) : TAKASHI NARA, et al.

It is certified that error appears in the above-identified patent and that said Letters Patent are hereby corrected as shown below:

Column 8, line 24, after "(pH 7.3 delete "s" and add --before sterilization). The main fermentation is carried out at 30°C for 4 days in an aeration stirring system (350 r.p.m. at aeration rate of 15 L./min.).

At the completion of culturing, the culture liquor is--

Signed and Sealed this

Sixteenth Day of October 1979

[SEAL]

Attest:

RUTH C. MASON
Attesting Officer

LUTRELLE F. PARKER
Acting Commissioner of Patents and Trademarks